US007925336B2

(12) United States Patent
Shvilkin et al.

(10) Patent No.: US 7,925,336 B2
(45) Date of Patent: Apr. 12, 2011

(54) DIFFERENTIATING ISCHEMIC FROM NON-ISCHEMIC T-WAVE INVERSION

(75) Inventors: Alexei V. Shvilkin, Chestnut Hill, MA (US); Mark E. Josephson, Brookline, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 0 days.

(21) Appl. No.: 12/572,747

(22) Filed: Oct. 2, 2009

(65) Prior Publication Data

US 2010/0222690 A1 Sep. 2, 2010

Related U.S. Application Data

(63) Continuation of application No. 11/625,538, filed on Jan. 22, 2007, now Pat. No. 7,620,449, which is a continuation of application No. 10/849,879, filed on May 21, 2004, now Pat. No. 7,194,299.

(51) Int. Cl.
*A61B 5/0452* (2006.01)
(52) U.S. Cl. ...................................... 600/517
(58) Field of Classification Search ............. 600/509, 600/515, 517
See application file for complete search history.

(56) References Cited

U.S. PATENT DOCUMENTS

| | | | |
|---|---|---|---|
| 5,148,812 A | 9/1992 | Verrier et al. |
| 5,213,106 A | 5/1993 | Lerner |
| 5,456,261 A | 10/1995 | Luczyk |
| 5,803,084 A | 9/1998 | Olson |
| 6,128,526 A | 10/2000 | Stadler et al. |
| 6,171,256 B1 | 1/2001 | Joo et al. |
| 6,507,753 B1 | 1/2003 | Xue et al. |
| 6,865,420 B1 | 3/2005 | Kroll |
| 7,194,299 B2 | 3/2007 | Shvilkin et al. |
| 7,620,449 B2 | 11/2009 | Shvilkin et al. |
| 2004/0064059 A1 | 4/2004 | Samuelson et al. |
| 2004/0111021 A1 | 6/2004 | Olson |

OTHER PUBLICATIONS

Okada, et al., "Clinical Implications of Isolated T Wave Inversion in Adults: Electrocardiographic Differentiation of the Underlying Causes of This Phenomenon," Tokyo, Japan; JACC, vol. 24, No. 3, pp. 739-745 (Sep. 1944).

Yokusoğlu, et al., "Assessing the Cause of T Wave Inversion in Precordial Leads With ECG Mapping," Journal of Electrocardiology, vol. 31, No. 2, pp. 125-132 (1998).

Takigawa, et al., "Significance of the Early Maximal Negative T Wave in Acute Anterior Myocardial Infarction," J. Cardiol. 32(4), pp. 235-245 (1998).

(Continued)

*Primary Examiner* — Carl H. Layno
*Assistant Examiner* — Jon-Eric C. Morales
(74) *Attorney, Agent, or Firm* — Sterne, Kessler, Goldstein & Fox P.L.L.C.

(57) ABSTRACT

A method of discriminating between ischemic and cardiac memory effects in a heart, comprising receiving electrocardiographic (ECG) data, calculating, from the ECG data, a direction of a T-wave vector, diagnosing ischemia if the T-wave vector is between about 75 degrees and about 200 degrees, and diagnosing cardiac memory if the T-wave vector is between about zero degrees and minus 90 degrees. Also presented is a system for discriminating between ischemic and cardiac memory effects in a heart comprising means for performing an electrocardiogram, means for calculating a direction of a T-wave vector, means for diagnosing ischemia if the T-wave vector is between about 90 degrees and 180 degrees, and means for diagnosing cardiac memory if the T-wave vector is between about zero degrees and minus 90 degrees.

12 Claims, 15 Drawing Sheets

OTHER PUBLICATIONS

Zimetbaum, et al., "Usefulness of ST-Segment Elevation in Lead III Exceeding That of Lead II for Identifying the Location of the Totally Occluded Coronary Artery in Inferior Wall Myocardial Infarction," Brief Reports, pp. 918-919 (1998).

Shvilkin, et al., "Evolution and Resolution of Long-term Cardiac Memory," Basic Science Reports, pp. 1810-1817 (May 12, 1998).

Gould, et al., "T-Wave Changes With Intermittent Left Bundle Branch Block," Communications to the Editor Clinical Case Reports, Angiology 31(1), pp. 66-68 (Jan. 1980).

De Zwaan, et al., "Characteristic Electrocardiographic Pattern Indicating a Critical Stenosis High in Left Anterior Descending Coronary Artery in Patients Admitted Because of Impending Myocardial Infarction," American Heart Journal, vol. 103, No. 4, part 2, pp. 730-736 (Apr. 1982).

Rosenbaum, et al., "Electrotonic Modulation of the T Wave and Cardiac Memory," The American Journal of Cardiology, vol. 50, No. 2, pp. 213-222 (Aug. 1982).

Nakajima, et al., "The Deeper the Negativity of the T Waves Recorded, the Greater Is The Effectiveness of Reperfusion of the Myocardium," Cardiology 87:91-97 (1996).

Plotnikov, et al., "Role of L-Type Calcium Channels in Pacing-Induced Short-Term and Long-Term Cardiac Memory in Canine Heart," Circulation, pp. 2844-2849 (Jun. 10, 2003).

Plotnikov, et al., "Interactions Between Antiarrhythmic Drugs and Cardiac Memory," Cardiovascular Research 50: 335-344 (2001).

Sasaki, et al., "Relation of ST-Segment Changes in Inferior Leads During Anterior Wall Acute Myocardial Infarction to Length and Occlusion Site of the Left Anterior Descending Coronary Artery," The American Journal of Cardiology, vol. 87, pp. 1340-1345 (Jun. 15, 2001).

Gould, et al., "Pacemaker-Induced Electrocardiographic Changes Simulating Myocardial Infarction," Chest, vol. 63, No. 5, pp. 829-832 (May 1973).

Herweg, et al., "Cardiac Memory After Radiofrequency Ablation of Accessory Pathways: The Post-ablation T Wave Does Not Forget the Pre-excited QRS," Journal of Interventional Cardiac Electrophysiology, vol. 3, No. 3, pp. 263-272 (1999).

Chatterjee, et al., "Electrocardiographic Changes Subsequent to Artificial Ventricular Depolarization," Brit. Heart J., 31:770-779 (1969).

De Zwaan, et al., "Angiographic and Clinical Characteristics of Patients With Unstable Angina Showing an ECG Pattern Indicating Critical Narrowing of the Proximal LAD Coronary Artery," Am. Heart J., 117:657-665 (Mar. 1989).

Hayden, et al., "Electrocardiographic T-wave Inversion: Differential Diagnosis in the Chest Pain Patient," Am. J. Emerg. Med., 20:252-262 (May 2002).

International Search Report from the United States Patent and Trademark Office for International Application No. PCT/US2005/17163, dated Aug. 22, 2006.

Written Opinion from the United States Patent and Trademark Office for International Application No. PCT/US2005/17163, dated Aug. 22, 2006.

Supplementary Partial European Search Report from the European Patent Office for European Application No. EP 05 75 0555, dated Aug. 2, 2010.

Shvilkin et al., "T Wave frontal plane direction differentiates precordial post-pacing from ischemic T wave inversions," *Heart Rhythm* 1:1 S163-S164, XP007914094 (May Supplement 2004).

LEAD AVF

L. FOOT

DIFFERENTIATING ISCHEMIC FROM NON-ISCHEMIC T-WAVE INVERSION

CROSS-REFERENCE TO RELATED APPLICATIONS

This application is a continuation of U.S. application Ser. No. 11/625,538, filed on Jan. 22, 2007, which issued as U.S. Pat. No. 7,620,449, which is a continuation of U.S. application Ser. No. 10/849,879, filed May 21, 2004, which issued as U.S. Pat. No. 7,194,299, the disclosures of which are incorporated herein in their entirety by reference thereto.

BACKGROUND OF THE INVENTION

1. Field of the Invention

The present invention relates to electrocardiography, and, more particularly, to a system and method for differentiating cardiac memory T-wave inversion from ischemic inversion.

2. Related Art

T-wave inversion (TWI) has a wide range of etiologies, from a normal variant to hypertrophic cardiomyopathy, pericarditis, and life-threatening myocardial ischemia. The majority of TWI falls in a category of "nonspecific ST-T-wave abnormalities" and accounts for 50% to 70% of abnormal tracings in general hospital populations. Interpretation of these ECGs is based primarily on correlation with available clinical data.

Post-pacing precordial T-wave inversions, known as cardiac memory, mimic anterior myocardial ischemia, and there are no established electrocardiographic criteria that adequately distinguish between the two. This phenomenon is well known to cardiologists. Cardiac memory is usually exhibited when a heart is paced for some period of time, and then the pacing is stopped. The cardiac memory effect usually depends on how long the heart was paced, and can last anywhere from a few hours to many weeks. Frequently, the T-wave following the pacing appears inverted. This is commonly referred to as T-wave inversion, or TWI. A similar TWI effect is frequently observed in ischemic patients. Specifically, post-pacing precordial T-wave inversion mimics anterior myocardial ischemia.

Cardiac memory is one of the benign causes of precordial TWI. ECG patterns of cardiac memory are manifested upon resumption of a sinus rhythm after a period of abnormal ventricular activation, such as ventricular pacing, transient left bundle branch block, ventricular arrhythmias, or WPW (Wolff Parkinson White syndrome). The most common cause of cardiac memory is ventricular pacing. Because T-wave changes of cardiac memory may persist for long periods of time after the pacing is discontinued, their causal relationship is often obscured. Although the benign nature of cardiac memory TWI is well established, no reliable diagnostic mechanisms have been described to differentiate pacing-induced cardiac memory from T-wave inversions resulting from anterior wall ischemia and infarction.

While the cardiac memory-induced T-wave inversion is a generally harmless phenomenon that usually disappears over time, ischemia is a serious problem, normally treated by coronary angioplasty, stenting or coronary bypass surgery. Ischemia is probably the most dangerous cause of T-wave inversion.

Because of the difficulty in distinguishing between the two causes of TWI, as well as in distinguishing causes of TWI in patients with pacemakers, many physicians, upon seeing T-wave inversion, are compelled to perform expensive and unnecessary catheterizations, angiograms, hospital admissions, time-consuming and costly evaluations to rule out ischemia, and other tests that would not be performed had the physician known that the T-wave inversion is due to cardiac memory, and not ischemia. Most physicians, in fact, when they see an inverted T-wave, assume the worst. Similarly, much of the automated diagnostic equipment, upon detection of an inverted T-wave, gives a diagnosis of possible ischemia.

Accordingly, there is a need in the art for a simple method of differentiating between benign cardiac memory-induced T-wave inversion, and ischemia-induced inversion.

SUMMARY OF THE INVENTION

The present invention relates to differentiating ischemic from non-ischemic T-wave inversion that substantially obviates one or more of the disadvantages of the related art.

Presented herein is a method of discriminating between ischemic and cardiac memory effects in a heart, comprising receiving electrocardiographic (ECG) data, calculating, from the ECG data, a direction of a T-wave vector, diagnosing ischemia if the T-wave vector is between about 75 degrees and about 200 degrees, and diagnosing cardiac memory if the T-wave vector is between about zero degrees and minus 90 degrees. Also presented is a system for discriminating between ischemic and cardiac memory effects in a heart comprising means for performing an electrocardiogram, means for calculating a direction of a T-wave vector, means for diagnosing ischemia if the T-wave vector is between about 90 degrees and 180 degrees, and means for diagnosing cardiac memory if the T-wave vector is between about zero degrees and minus 90 degrees.

Additional features and advantages of the invention will be set forth in the description that follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE FIGURES

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Reference will now be made in detail to the preferred embodiments of the present invention, examples of which are illustrated in the accompanying drawings.

Figure 1A:
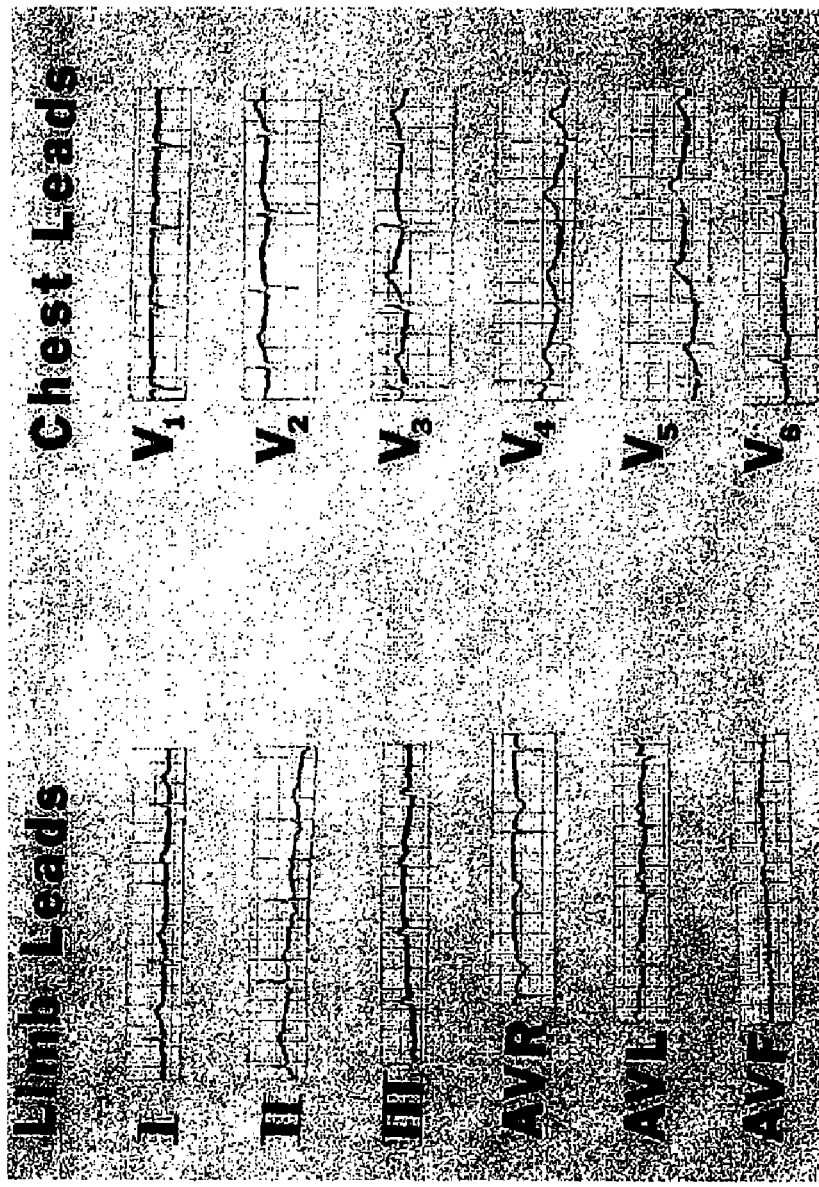
FIGS. 1A-1F illustrate placements of ECG leads.
Figure 1B:
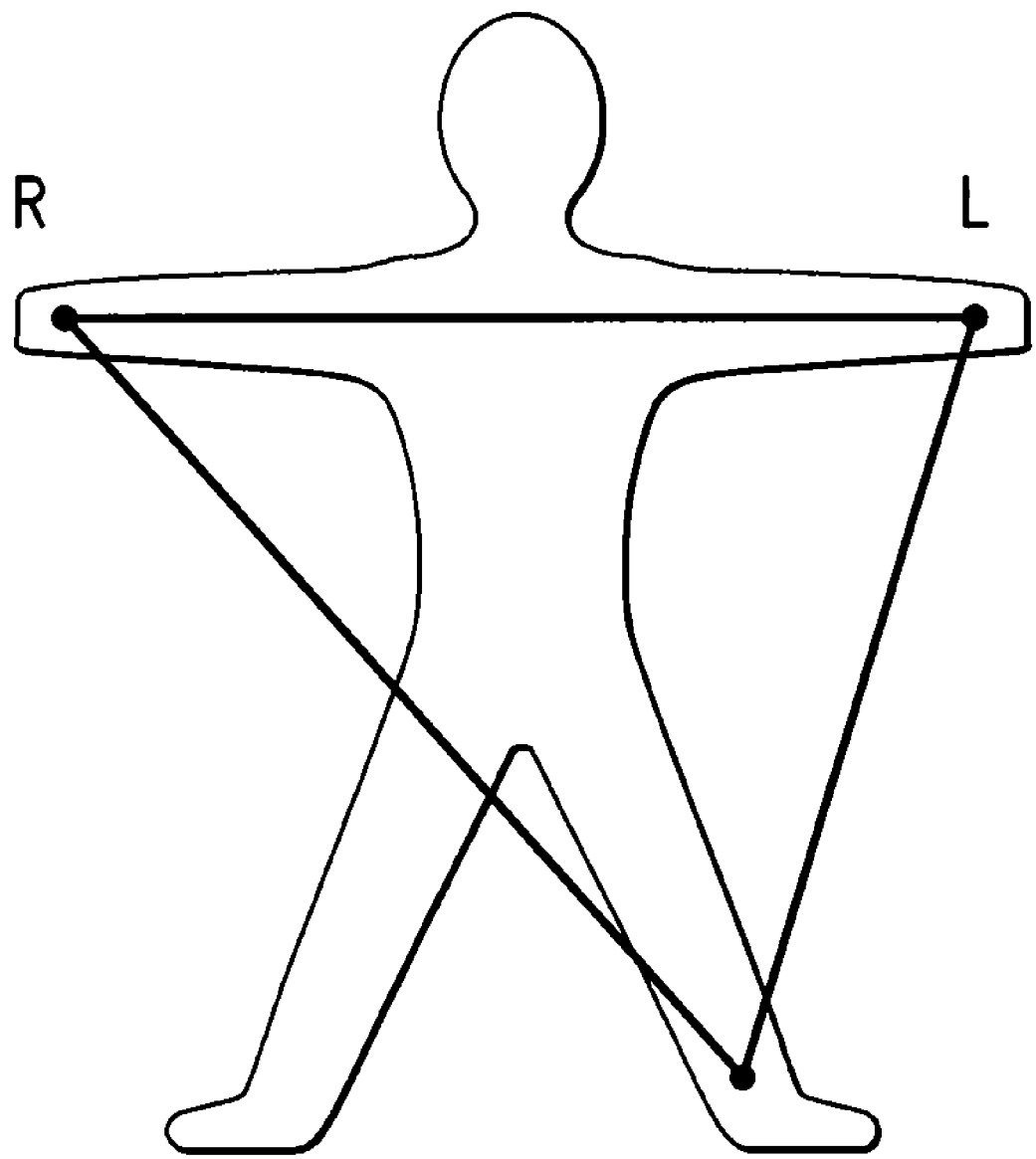
Figure 1C:
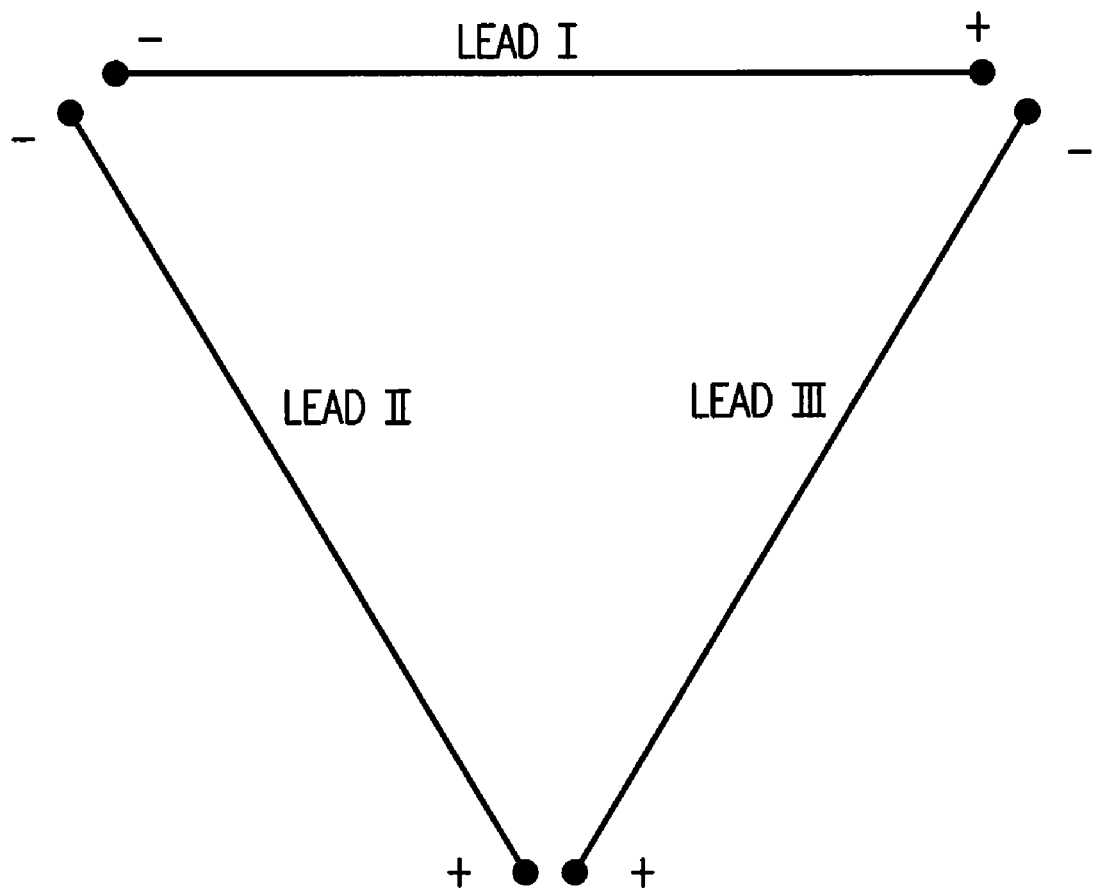
Figure 1D:
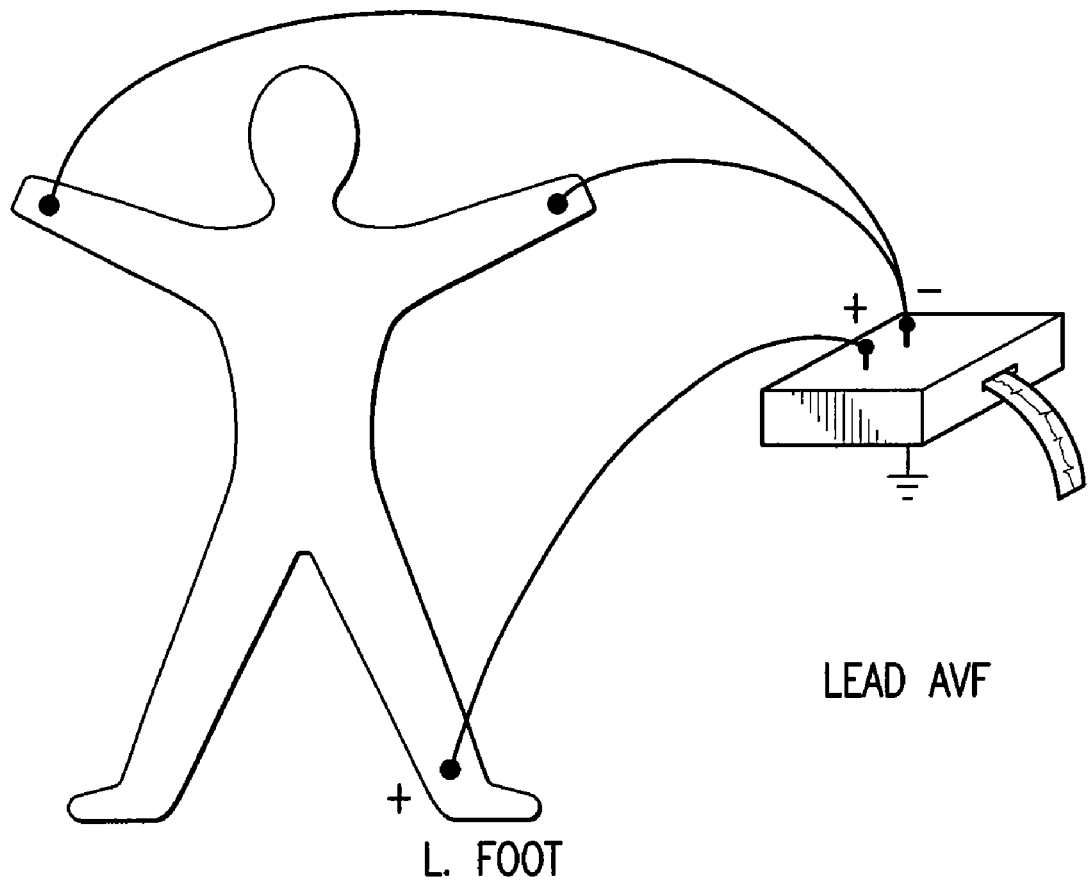
Figure 1E:
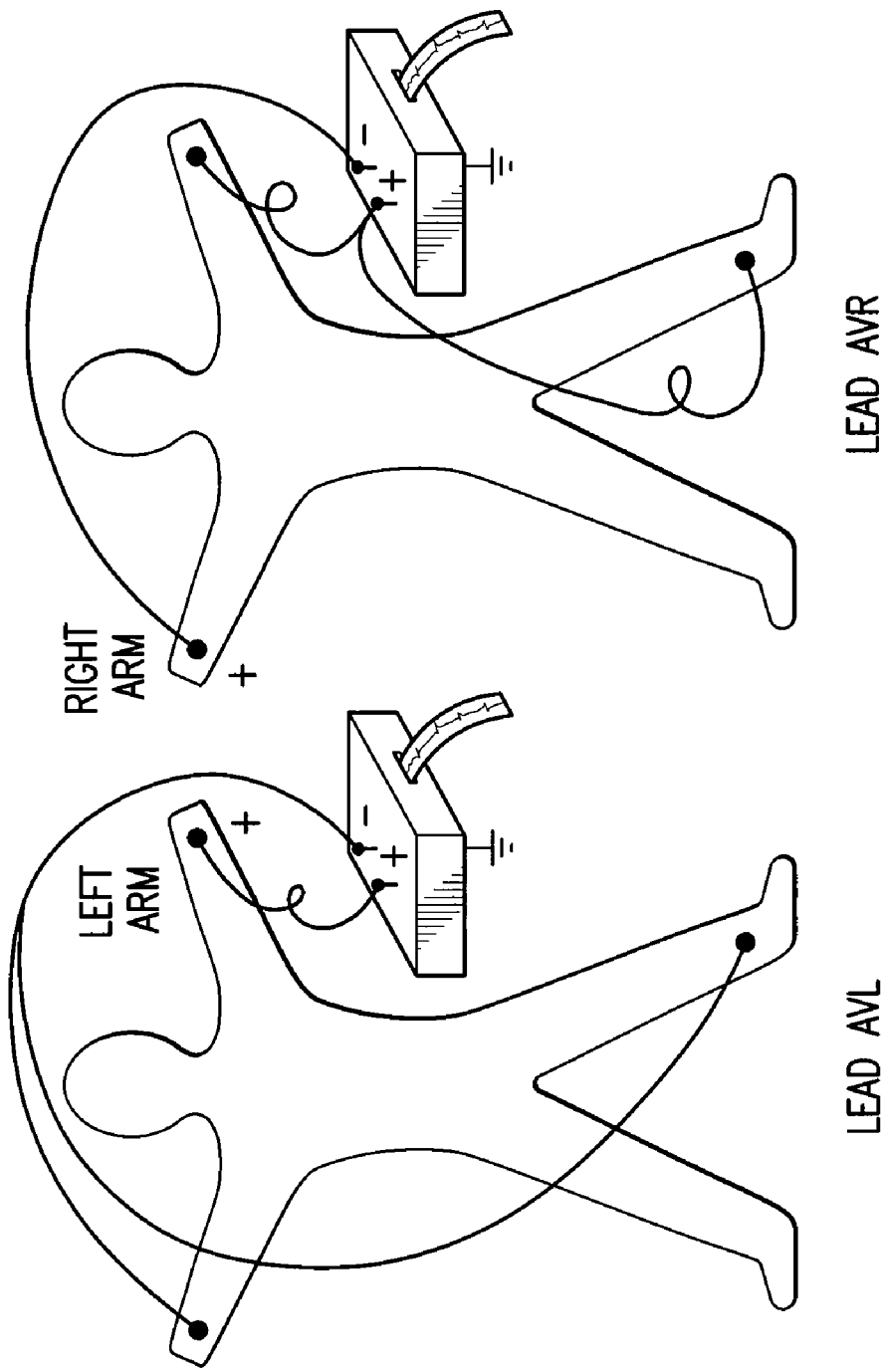
Figure 2:
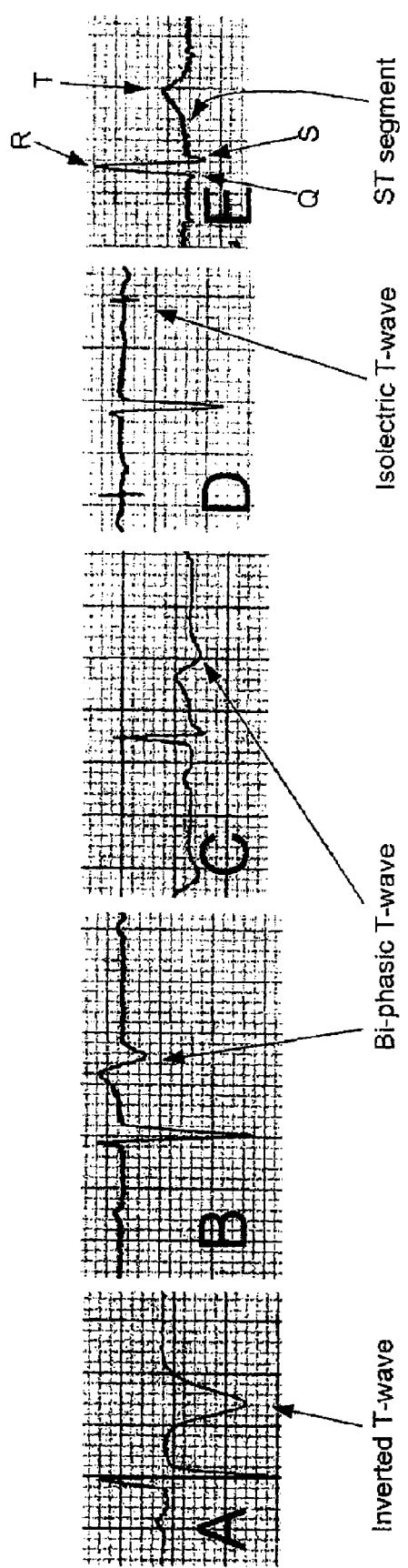
FIG. 2 shows a classification of T-waves.

FIGS. 1A-1E illustrate the terminology used in cardiography, and FIG. 2 shows exemplary electrocardiogram (ECG) traces.

Figure 1F:
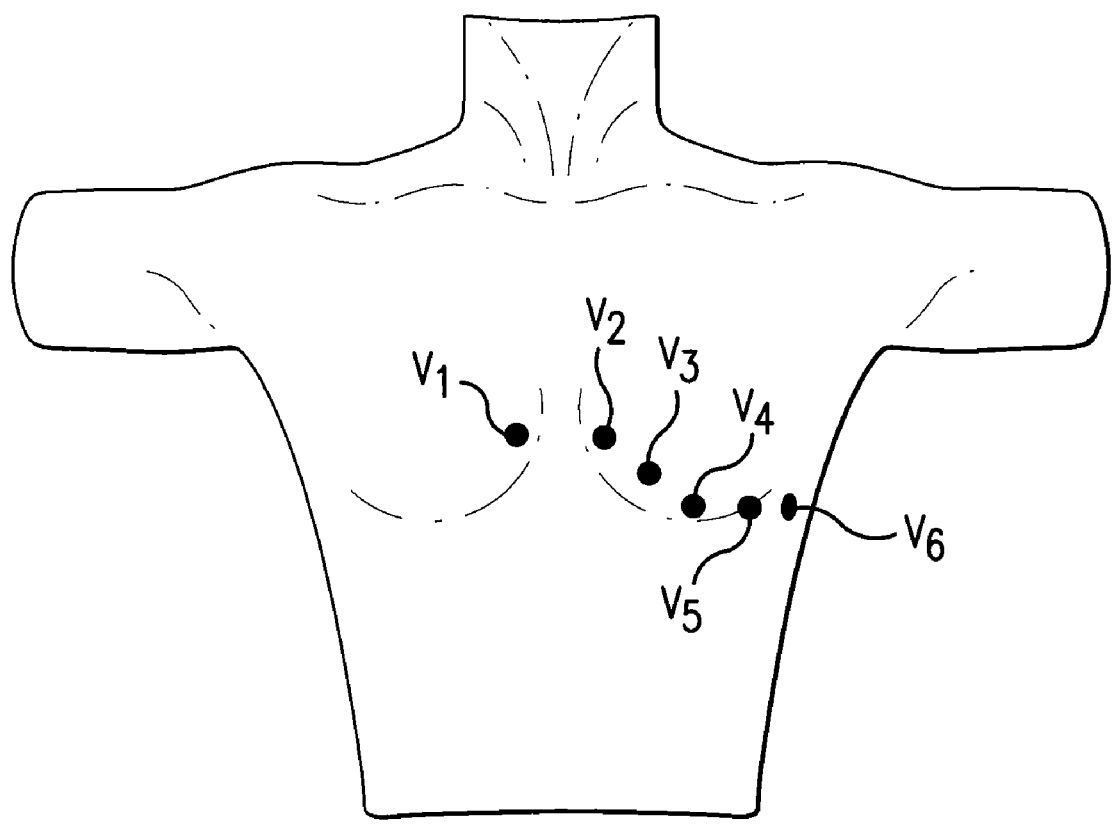

FIG. 1A illustrates representative ECG waveforms taken from the twelve standard surface leads, the six limb leads numbered I, II, III, aVR, aVL and aVF, and the six chest leads, also known as precordial leads, $V_1$-$V_6$. FIG. 1B shows positioning of the limb leads I, II and III. FIG. 1C illustrates the connections for the limb leads I, II and III. Lead I has a horizontal axis, going from right to left. Lead aVF has a vertical axis, and goes top to bottom. Leads I and II are approximately 30° apart. Lead II is approximately 60° down from right to left. FIG. 1D illustrates the connections for limb lead aVF. FIG. 1E illustrates the connections for the limb leads aVL and aVR. FIG. 1F illustrates the placements locations of the precordial leads $V_1$-$V_6$. Lead aVF points straight down, or towards six o'clock.

Typical diagnostic equipment that is used in vector cardiography gives an angle measurement of the T-wave vector (and usually not the magnitude, since it is the vector direction that is of primary interest). The reader is referred to, e.g., Dale Dubin, Rapid Interpretation of EKG's, $4^{th}$ ed., Cover Publishing Co., 1989, which is incorporated by reference herein, for a more complete discussion of lead placements. Also, the three arteries in the heart are usually abbreviated as the LAD artery (left anterior descending), the circumflex artery (LCX), and the right coronary artery (RCA).

Panels A-C in FIG. 2 show examples of negative inverted T-waves (-0.8; -0.2; -0.1 mV, respectively). Panel D shows an isoelectric T-wave (0 mV). Panel E shows a (normal) positive T-wave (+0.2 mV). As shown in FIG. 2, panel E, in a healthy heart, the QRS complex is followed by the S-T segment, and then followed by a positive T-wave.

Based on cardiac memory definition (post-pacing sinus rhythm T vector approaching direction of the paced QRS), the inventors hypothesized that cardiac memory resulting from right ventricular pacing would have a frontal T vector direction different from that of anterior ischemic TWI, thereby enabling to discrimination between the two.

Two groups of patients were studied. The cardiac memory group consisted of thirteen patients undergoing permanent pacemaker implantation who had sinus rhythm with 1:1 atrioventricular (AV) conduction at physiologic heart rates. None of the patients had clinical, ECG or biochemical evidence of active ischemia. Cardiac memory was induced by one week of AV pacing with a short atrioventricular delay. The extent of the atrioventricular delay was adjusted individually to allow ventricular activation to proceed completely from the endocardial pacemaker electrode positioned in the right ventricular apex. At one week, a 12-lead ECG was recorded after the pacemaker was reprogrammed in AAI mode. This ECG was used for analysis.

T-wave axis, polarity, and amplitude on a 12-lead ECG were compared between cardiac memory and ischemic patients. The cardiac memory group included eleven patients with no clinical signs of ischemia, and were sequentially paced for one week after permanent pacemaker implantation. The ischemic patient group consisted of 47 patients with precordial TWI undergoing LAD (left anterior descending) artery intervention for non-ST elevation myocardial infarction. Table 1 below shows the baseline patient data.

TABLE 1

Distribution of TWI by infarct-related artery in ischemic group.

| Vessel involved | TWI | No TWI | Excluded | Total |
|---|---|---|---|---|
| LAD | 28 (47%)* | 31 | 20 | 79 |
| Proximal | 16 (57%) | 12 | 7 | |
| Mid, D1 | 12 (44%) | 15 | 10 | |
| Distal | 0‡ | 4 | 3 | |
| LCX | 12 (21%) | 44† | 17 | 73 |
| RCA§ | 7 (11%) | 56 | 13 | 76 |
| Total | 47 (26%) | 131 | 50 | 228 |

*$p < 0.05$ vs. LCX and RCA groups
†Including 5 patients with isolated TWI in leads I, aVL
‡$p < 0.05$ vs. other LAD locations
§29 patients with inferior TWI only, 1 patient with TWI in leads I, avL Patients with preexisting ECG abnormalities were excluded, e.g., patients with secondary TWI, such as preexisting left bundle branch block or LVH (left ventricular hypertrophy) manifesting negative T-waves in leads I and aVL, atrial fibrillation and ST elevation infarcts. Patients with voltage criteria for left ventricular hypertrophy were also excluded, unless upright precordial T-waves were documented on prior tracings.

The ischemic patient group had ischemic precordial TWI due to unstable angina/non-Q wave myocardial infarction, identified retrospectively among patients undergoing percutaneous coronary intervention (PCI) on one of the three major coronary arteries (LAD, LCX, RCA). If TWI was present on more than one ECG, the earliest ECG from index admission was used for analysis.

Burdick Space Lab and Marquette MAC-5000 electrocardiographs were used to record the ECGs, which were analyzed manually. T-wave amplitude was measured in each lead at T-wave peak/nadir to the baseline determined by T-P segment. In case of biphasic T-waves (see, e.g., panel C in FIG. 2), the most negative deflection was taken for the peak and T-wave was classified as negative. T-wave was classified as isoelectric (amplitude=0) if both positive and negative components were present with an amplitude of less than 0.05 mV. QT was measured manually over three consecutive RR intervals in leads available on the rhythm strip (typically, lead II or lead $V_5$) and the results were averaged. Frontal plane QRS and T vector angles were obtained from standard automated ECG printouts.

Clinical data was obtained from electronic medical records. Left ventricular ejection fraction, determined as a part of routine clinical management by echocardiograpy, or contrast left ventriculography, was used for analysis if it was performed during the index admission (ischemic group) or within a year prior to the pacemaker implant (cardiac memory group).

Location of the culprit lesion within LAD system (proximal, mid) and involvement of the first diagonal branch (D1 branch) was determined from angiographic reports and confirmed by visual analysis of digital angiographic films (if report statements were unclear).

Continuous variables were expressed as mean±SEM and compared analysis of variance. Nominal data were compared using a Chi-square test. Angular variables (frontal plane QRS and T-wave axes) were compared using Watson-Williams F test. P values of less than 0.05 were considered statistically significant.

Baseline group characteristics are presented in Table 2 below. Male/female ratio did not differ between groups. Patients in this ischemic group were, on average, younger than in the cardiac memory group (65.3 vs. 72.5 years old, p<0.05). Prior ECGs were available in 13/13 cardiac memory and 19/47 ischemic patients. There was no statistically significant differences in the prevalence of baseline ECG abnormalities between ischemic and cardiac memory groups.

TABLE 2

Baseline Clinical Data

| Group | ischemia | Cardiac memory |
|---|---|---|
| N | 47 | 13 |
| Male, n (%) | 28 (60) | 6 (46) |
| Age, yrs | 65.3 ± 2.0 | 72.5 ± 3.0* |
| Prior history of MI, n (%) | 12 (25.5%) | 3 (23%) |
| History of CABG | 8 (17%) | 2 (15%) |
| Prior ECG Available | 19/47 | 13/13* |
| Precordial TWI | 4/19 | 0/13 |
| Right bundle branch block | 1/19 | 3/13 |
| Q waves | 4/19 | 2/13 |

*p < 0.05 script indicates the lead in which the T-wave was observed), whereas cardiac memory uniformly showed a TWI pattern $|T_{III}|>T_{II}|$. T-wave patterns in limb leads were consistent with left superior frontal plane T vector in cardiac memory and rightward in ischemic patients.

Sixteen patients (57%) had a proximal LAD lesion with ischemic territory involving the D1 branch. Twelve patients (44%) had a mid-LAD lesion or an isolated D1 lesion. No significant differences were found in the magnitude of T-wave inversions between proximal and mid LAD lesions as well as between patients with and without D1 territory involvement.

CK (creatine kinase) levels were available in 27/28 LAD ischemic patients. In seven patients, CK MB (creatine kinase myocardial branch) testing was not performed, as the total CK was <100 IU/l. Ten patients had CK MB within the normal range (<10 ng/ml), seventeen patients (61%) had CK MB elevation ranging from 13 to 366 ng/ml (median 46 ng/ml). Twenty three patients (82%) had troponin I or T results available. Of those, 26 patients (93% of the LAD ischemic patients) had troponin elevation (range 0.2 to >50, median 4.2 ng/ml). All but one patient had results of either CK MB or troponin available.

No significant difference was observed in T-wave amplitudes in any of the limb leads in patients with and without CK MB elevation (<10 ng/ml). Comparison of precordial T-wave amplitudes showed a trend for deeper T-waves in patients with normal CK MB, compared to those with positive enzyme, with differences in leads $V_3$ and $V_5$ reaching statistical significance (see Table 3 below).

TABLE 3

Precordial T-wave inversion amplitude in ischemic patients with (MB+, n = 17) and without (MB−, n = 10) CK MB elevation.

| | Leads | $V_1$ | $V_2$ | $V_3$ | $V_4$ | $V_5$ | $V_6$ |
|---|---|---|---|---|---|---|---|
| T-wave amplitude, mV | MB(+) | 0.08 ± 0.04 | −0.18 ± 0.08 | −0.17 ± 0.06 | −0.25 ± 0.05 | −0.18 ± 0.05 | −0.07 ± 0.04 |
| | MB(−) | 0.04 ± 0.06 | −0.24 ± 0.13 | −0.45 ± 0.17* | −0.42 ± 0.11 | −0.26 ± 0.10* | −0.15 ± 0.09 |
| p | | 0.7 | 0.2 | 0.02 | 0.07 | 0.03 | 0.07 |

*p < 0.05. No relationship was found between EF and the degree of TWI in the ischemic group.

All patients in the study had endocardial right ventricular apex lead implants. Other positions within the right ventricle can produce different pacing QRS vectors with different resulting memory T-waves. Endocardial pacemaker implants utilize the right ventricular apex, mid-septum, or outflow tract as sites for the ventricular electrode. The QRS complex produced by pacing from any of these sites usually has a left axis with varying degree of superior (right ventricle apex) or inferior (right ventricle outflow tract) angulation. Therefore, post-pacing TWI will always assume a left frontal axis, no matter where in the right ventricle the pacing lead is situated. However, with right ventricle outflow tract pacing, one would not usually see deep T-wave inversions in inferior leads, which are considered typical for post-pacing TWI.

T-wave morphology, polarity and amplitude in precordial leads were similar between the two patient groups. In the cardiac memory group, T-waves in both leads I and aVL were positive or isoelectric in 13/13 patients vs. 0/47 in ischemia (p<0.001). If present, inferior TWI in ischemic patients invariably demonstrated a TWI $|T_{II}|>T_{III}|$ pattern (the sub- The inventors have discovered that cardiac memory and ischemia that cause indistinguishable precordial TWI can nonetheless be differentiated on the basis of frontal plane T vector direction. Cardiac memory results in frontal T vector projection were opposite to those of anterior ischemia. A combination of positive $T_{aVL}$ and non-inverted $T_1$ was present in all cardiac memory patients and in none of the ischemic patients, thus discriminating cardiac memory from ischemia. The presence of positive T-waves in leads I and aVL provides evidence against ischemic etiology of precordial TWI.

Figure 3A:
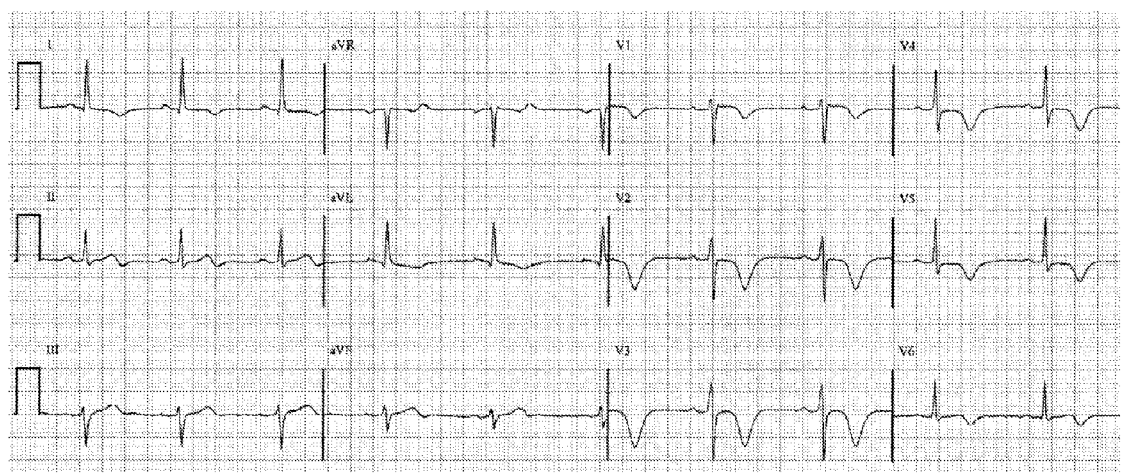
FIG. 3A shows a representative ECG of an ischemic patient.
Figure 3B:
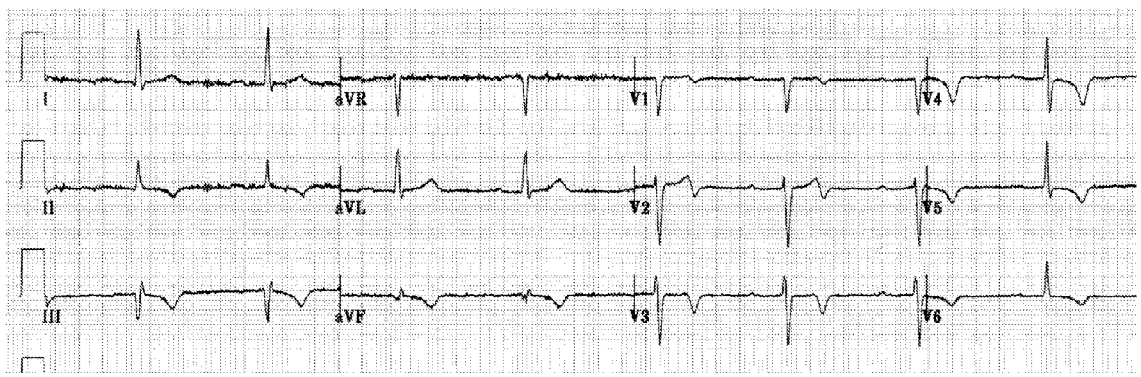
FIG. 3B shows a representative ECG of a cardiac memory patient.

Representative examples of ECGs are depicted in FIGS. 3A-3B. FIG. 3A shows a representative ECG of an ischemic patient, while FIG. 3B shows a representative ECG of a cardiac memory patient. Both cardiac memory and ischemia traces demonstrate deep T-wave inversion in the precordial leads $V_1$-$V_6$ of similar magnitude and morphology. In addition to precordial TWI, the cardiac memory patient demonstrates deep inferior T-wave inversion. However, a biphasic T-wave is also present in lead II in the ischemia tracing. An important difference between recordings is seen in leads I and aVL, in which ischemia shows T-wave inversions, whereas cardiac memory manifests positive T-waves.

Electrocardiographic data is summarized in Table 3 below. The heart rate was faster in the cardiac memory group ($p<0.05$) due to predominant atrial pacing in this group. Both QT and QTc intervals were not statistically different between groups.

TABLE 3

Electrocardiographic Data

| Group | ischemia | | | Cardiac memory |
|---|---|---|---|---|
| | LAD | LCX | RCA | |
| HR, $min^{-1}$ | 69.4 ± 2.1 | 74.2 ± 3.1 | 66.9 ± 3.6 | 71.7 ± 3.7 |
| QT, ms | 440 ± 10 | 415 ± 11 | 438 ± 10 | 417 ± 10. |
| QTc | 415 ± 14 | 377 ± 16 | 418 ± 15 | 371 ± 11.4 |
| Number of precordial leads with TWI | 4.0 ± 0.3 | 3.25 ± 0.5* | 2.9 ± 0.3* | 4.8 ± 0.3 |
| Maximal precordial TWI, mV | −0.45 ± 0.06 | −0.21 ± 0.10* | −0.26 ± 0.11* | −0.53 ± 0.06 |
| QRS frontal axis, degrees | +20 ± 7 | +6 ± 11 | 6 ± 46 | +18 ± 12 |
| T wave frontal axis, degrees | +128 ± 10* | +146 ± 15* | −98 ± 30 | −70 ± 5* |

*$p < 0.05$ compared to cardiac memory group

T-wave amplitudes measured at the peak/nadir of T-wave in precordial leads were indistinguishable between CM and ISC-LAD groups (see FIG. 4, discussed below, $p>0.05$ for all precordial leads $V_1$-$V_6$). In contrast, all the limb leads (with the exception of aVR), showed highly significant differences in T-wave amplitude as well as polarity between groups (see FIG. 5, discussed below). The most dramatic difference was observed in lead aVL, where all cardiac memory patients had positive T-waves compared to only one ischemic patient ($p<0.01$), whose T-wave in lead I was negative. Positive T-wave in lead I was observed in 11 out of 13 cardiac memory patients, in the remaining two, the T-wave was isoelectric, and none had negative T-waves No ischemic patients had the combination of positive $T_{avL}$ and non-inverted (positive or isoelectric) $T_1$. This is in contrast to all observed cardiac memory patients.

The inventors hypothesize that, when a patient is implanted with a pacemaker, one of the leads goes into the right ventricle. Pacing the heart from this lead produces negative QRS complexes in all the precordial leads $V_1$-$V_6$. This is the reason why the T-waves are inverted when the pacing is stopped. By the same token, cardiac memory produces positive T-waves in leads I and aVL. Ischemia gives the same result in the precordial leads ($V_1$-$V_6$), while it gives the opposite result in leads I and aVL. This is also due to the fact that ischemia typically affects the left ventricle, and not the right ventricle. Ischemia therefore gives negative T-waves in leads I and aVL. In other words, in a patient with cardiac memory-induced T-wave inversion, the ECG on leads I and aVL looks normal.

Figure 4:
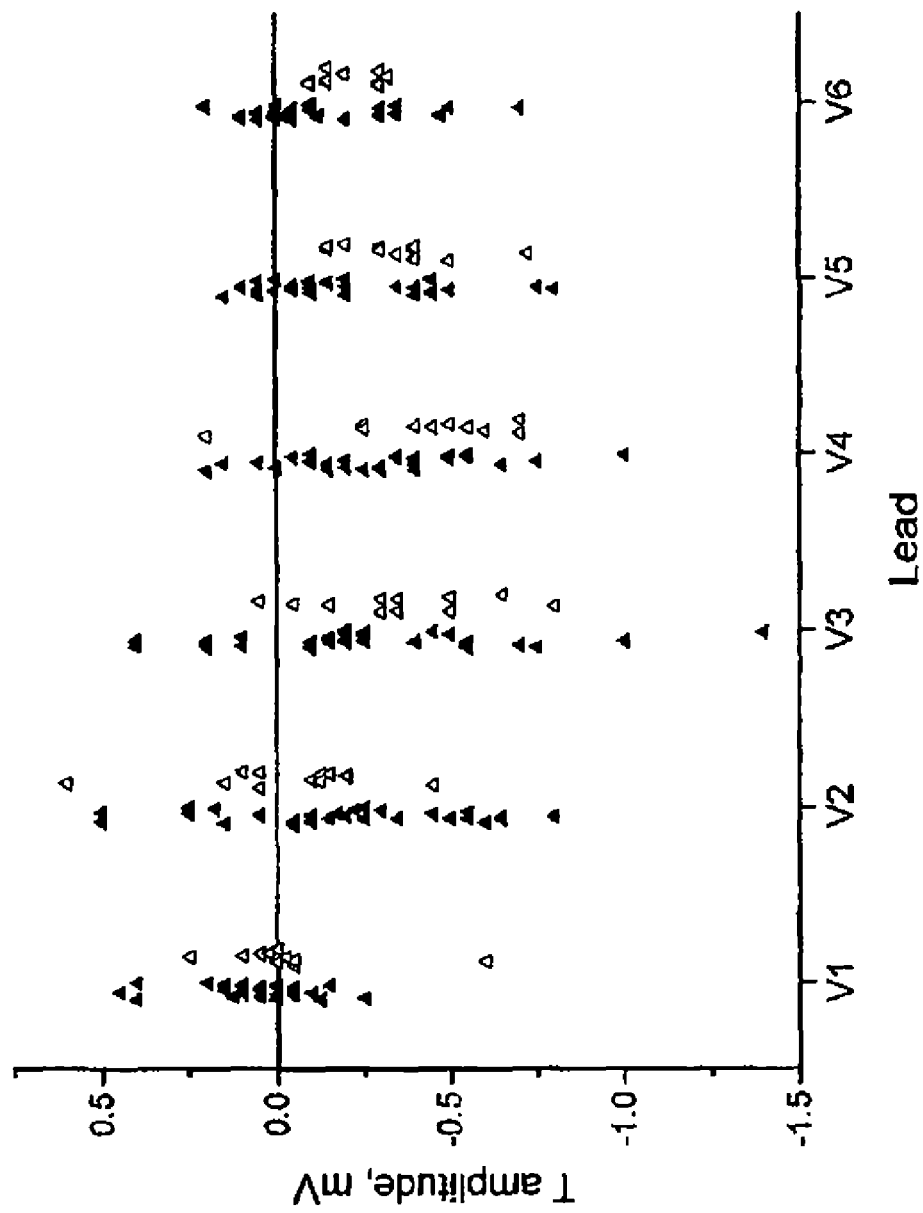
FIG. 4 shows T-wave amplitude in the precordial leads ($V_1$-$V_6$).
Figure 5:
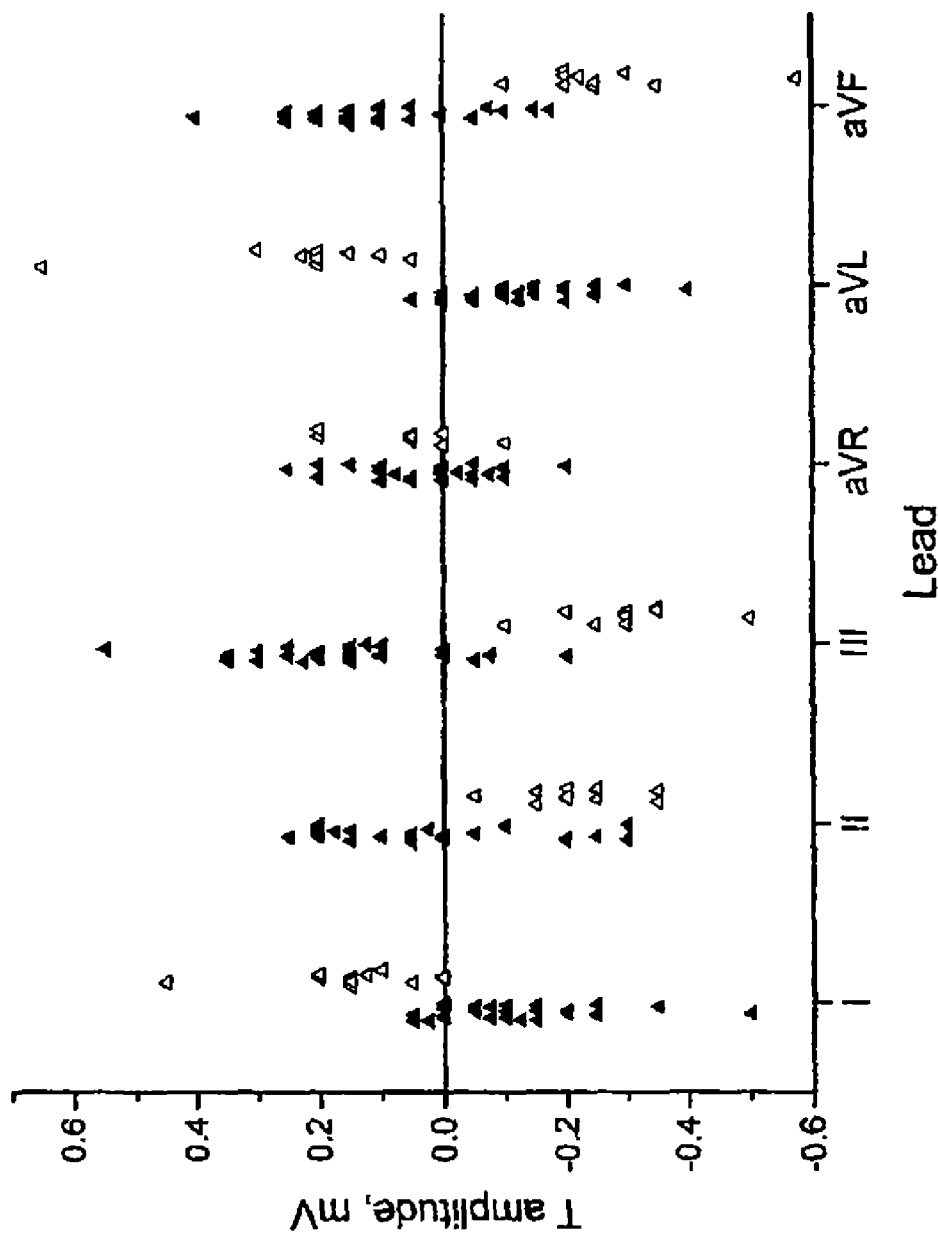
FIG. 5 shows T-wave amplitude in the limb leads.

FIGS. 4 and 5 illustrate the data distribution for two patient populations, the LAD ischemic patients and the cardiac memory patients. The open triangle symbols represent the cardiac memory patients, and the closed (dark) triangle symbols represent the ischemic patients. FIG. 4 shows T-wave amplitude in the precordial leads $V_1$-$V_6$. No significant difference in amplitude is observed between groups. The T-wave negativity is particularly pronounced for leads $V_2$-$V_6$, with both groups exhibiting T-wave negativity.

FIG. 5 shows T-wave amplitude in the limb leads. Again, closed symbols are LAD ischemic patients, open symbols are cardiac memory patients. The difference in amplitude between groups is statistically significant ($p<0.05$ for all leads except aVR). As may be seen in FIG. 5, leads I and aVL exhibit the greatest contrast in the T-waves between the two groups. With regard to both leads I and aVL, the T-waves for the cardiac memory group are either flat or positive, while the T-waves for the ischemic group are typically negative, and generally less than +0.05 millivolts. Additionally, ECG from lead III may also be used to discriminate, although not to the same extent, but lead III T waves are particularly useful for discriminating RCA ischemia TWI from cardiac memory.

As shown in the tables and FIGS. 4-5, all cardiac memory patients had inverted T-waves in leads III with $T_{III}$ deeper than $V_1$-$V_6$.

The reason for the observed differences in limb lead T-wave amplitudes between groups is best appreciated via vectorcardiography. While the frontal plane QRS axis in both groups was almost identical (see Table 3 above), T-wave axes differed dramatically (see also FIG. 6), with the mean angle difference between groups approaching 180 degrees (+128 vs. about 71 degrees, for ischemic and cardiac memory groups, respectively, $p<0.01$).

Figure 6:
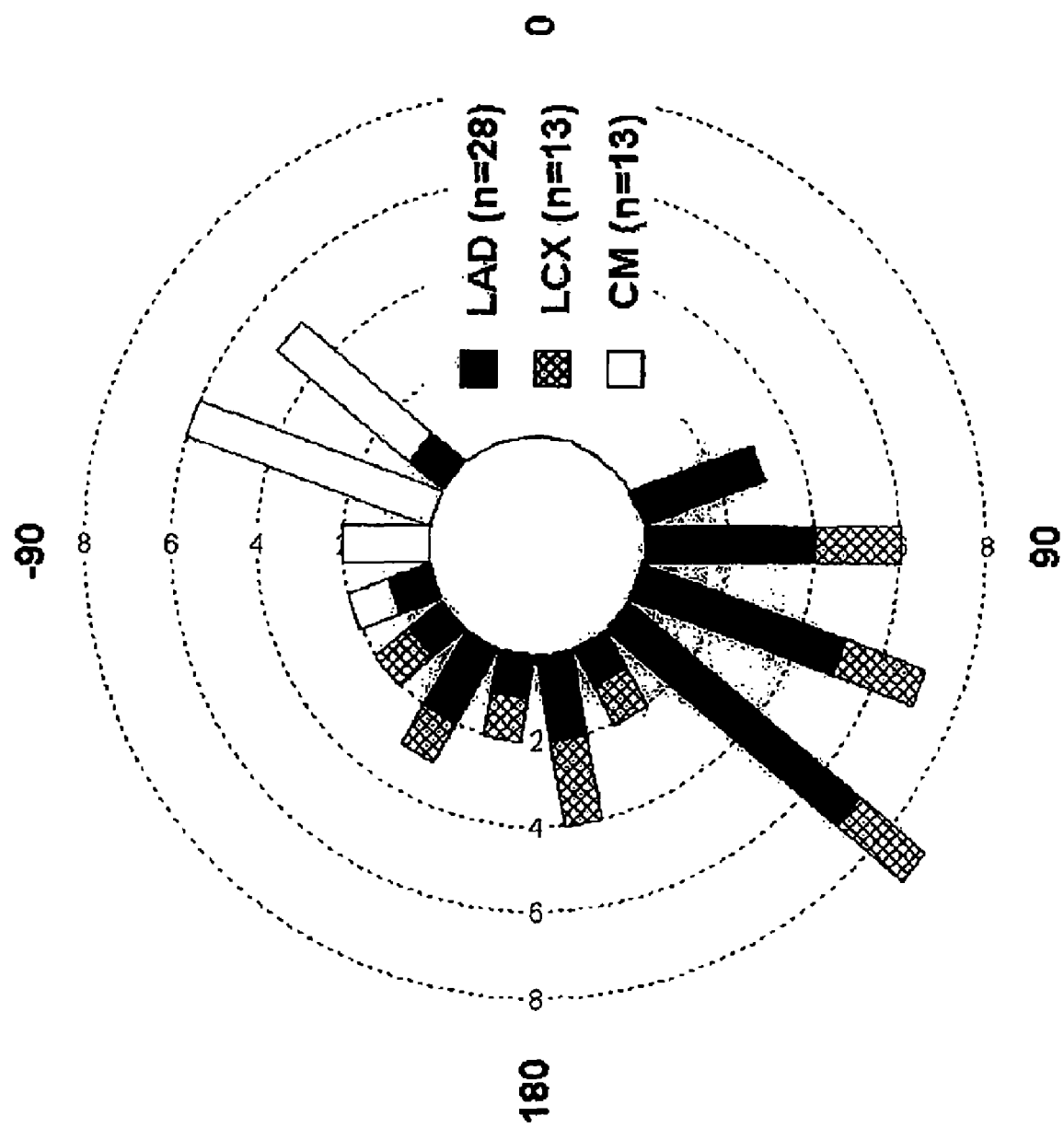
FIG. 6 shows a circular histogram of frontal plane T axes distribution.

FIG. 6 is a polar histogram representing the information summarized in FIGS. 4 and 5. FIG. 6 shows a polar histogram of frontal plane T axes distribution. Filled bars are LAD ischemic patients, hatched bars are LCX ischemic patients, and open bars are cardiac memory patients. Each circular dashed line represents two patients. The histogram shows that a typical cardiac memory patient will show T-wave vectors generally in the approximately −90° direction. Ischemic patients, on the other hand, will show T-wave vectors generally between about +90° (probably from about as low as +75°) and about +180° (probably up to about +200°). The difference in T vector direction between groups is statistically significant ($p<0.01$).

In the limb leads, the same principle was observed. In the majority of LAD and LCX patients, T waves were negative in leads I and aVL. Three LAD/LCX patients had positive T waves in lead I, one patient—in lead aVL and none in both leads. In vector terms, this translated into left-to-right direction of the T axis (see Table 4 below and FIG. 6). Limb lead TWI pattern in RCA group was variable, depending on the relative involvement of lateral and inferior leads. Four patients with predominantly lateral precordial TWI (maximal precordial TWI amplitude>maximal inferior lead TWI amplitude) demonstrated TWI in leads I and/or aVL and left-to-right T vector axis similar to LAD and LCX groups. Three patients with predominantly inferior lead TWI (maximal amplitude precordial TWI<TWI$_{III}$) had positive T waves in leads I and aVL.

T vector in cardiac memory group followed the direction of the paced QRS complex. RVA pacing produced QRS that was predominantly negative in precordial leads, negative in inferior leads and invariably positive in leads I and aVL. As a result, diffuse TWI in the precordial and inferior leads and positive T waves in leads I and aVL were characteristic for cardiac memory. This translated into left superior T vector axis opposite in direction to that of LAD, LCX and part of RCA groups. With the exception of the patient with post-implant pericarditis, all cardiac memory patients demonstrated maximal precordial TWI>TWI$_{III}$.

Cardiac memory vs. LAD/LCX: The most dramatic difference between groups was observed in lead aVL, where all cardiac memory patients had positive T waves compared to only one ischemia patient, whose T wave in lead I was negative. Positive T wave in lead I was observed in 11/13 cardiac memory patients; in the remaining two (both of whom had prior inferior wall MI) T-waves were isoelectric, and none had negative T waves. The combination of positive T wave in lead aVL and positive/isoelectric T in lead I (criterion I+aVL) was seen in all cardiac memory patients and none of LAD/LCX patients (see Table 4 below).

Cardiac memory vs. RCA: Four out of 7 RCA patients conformed to the pattern of LAD/LCX TWI and criterion I+aVL discriminated them from cardiac memory. The remaining 3 RCA patients with positive T$_1$ and T$_{aVL}$ had maximal precordial |TWI|<|TWI$_{III}$| in contrast to all but one cardiac memory patients.

or greater. The signal is generally calibrated to 10 millimeters per millivolt on the ECG printout.)

One embodiment of the invention may be implemented using a standard diagnostic ECG, such as available from Burdick Space Lab or Marquette, modified to differentiate the two types of TWI according to the principles described above. Alternatively, although the discussion above is primarily in terms of using an external ECG (e.g., a standard 12-lead ECG), the invention is also applicable to implantable devices. For example, implantable cardiac defibrillators (ICDs) usually have three implanted electrodes: a pacing electrodes in the right ventricle, a coil (defibrillator) electrodes in the superior vena cava, and the ICD "can" itself (usually located in the pectoral area under the skin). Using these electrodes (and, optionally, using additional electrodes as well, if available), the implantable device can "reconstruct" the direction of the T-wave vector, and, based on the direction of the T-wave vector, as discussed above, discriminate between cardiac memory TWI and ischemic TWI. Alternatively, the implantable device can perform mathematical operations on the data from the leads that generally correspond to discriminating between the two types of TWI in the manner discussed above, without directly calculating the T-wave vector direction.

Figure 8:
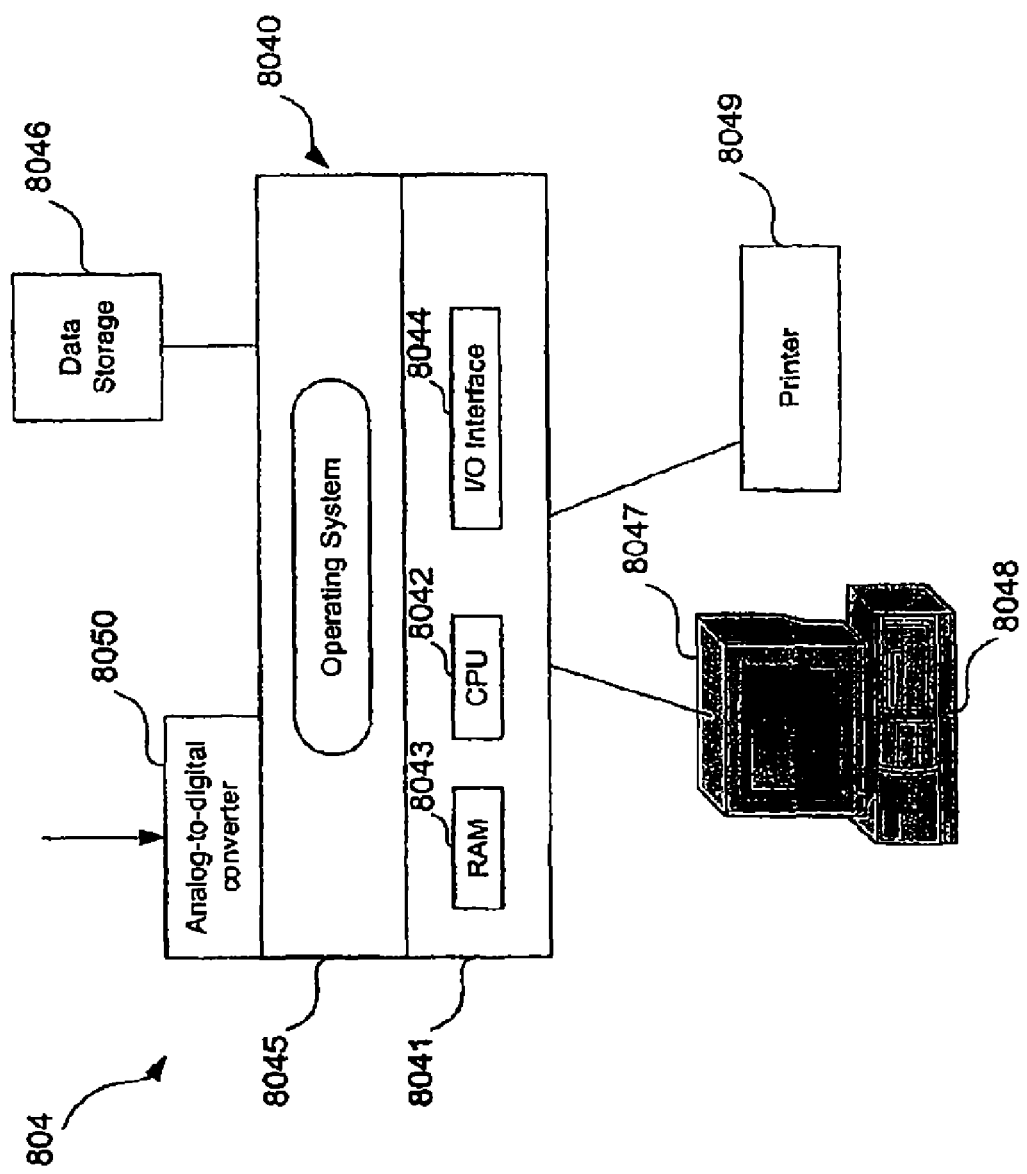
FIG. 8 shows an exemplary hardware system for differentiating TWI.

Another exemplary hardware system for differentiating TWI is shown in FIG. 8. Referring to FIG. 8, an ECG processing system 804 is described. ECG processing system 804 includes a programmed microcomputer 8040 equipped with an analog-to-digital (A/D) conversion board 8050. The steps of the method are performed using a software program written in, e.g., C programming language. The program follows the steps set forth above. It is believed that any skilled programmer would have no difficulty writing the code necessary to perform the steps of this invention.

TABLE 4

Lead distribution of TWI in ischemic and cardiac memory groups, n (%).

| Group | ischemia | | | | | | | |
|---|---|---|---|---|---|---|---|---|
| Lead | LAD | (n = 28) | LCX | (n = 12) | RCA | (n = 7) | CM | (n = 13) |
| V1 | 8 | (29) | 1 | (8) | 0 | | 5 | (39) |
| V2 | 21 | (75) | 5 | (42) | 0* | | 8 | (62) |
| V3 | 22 | (79) | 5 | (42) | 1 | (14)* | 12 | (92) |
| V4 | 24 | (86) | 7 | (58) | 6 | (86) | 12 | (82) |
| V5 | 21 | (75) | 10 | (83) | 6 | (86) | 13 | (100) |
| V6 | 16 | (57)* | 11 | (92) | 7 | (100) | 13 | (100) |
| I | 20 | (71)* | 11 | (91)* | 4 | (57)* | 0 | |
| II | 8 | (29)* | 5 | (42)* | 6 | (86) | 13 | (100) |
| III | 3 | (11)* | 2 | (17)* | 4 | (57)* | 13 | (100) |
| aVR | 10 | (36)* | 0 | | 1 | (14) | 1 | (8) |
| aVL | 23 | (82)* | 11 | (92)* | 2 | (29) | 0 | |
| aVF | 6 | (21)* | 4 | (33)* | 5 | (71) | 13 | (100) |
| (I + aVL)** | 0* | | 0* | | 3 | (43)* | 13 | (100) |
| (I + aVL) and maximal precordial TWI > TWI III | | | | | 0* | | 12 | (92) |

*p < 0.05 with cardiac memory group
**(I + aVL) - positive T wave in lead aVL, positive or isoelectric T wave in lead I.

Based on the obtained results, it is generally sufficient to look at leads I and aVL for LAD and LCX ischemia, and to consider the most negative component of the T-wave. If lead I shows a positive T-wave, and lead aVL shows positive or flat T-wave, while the precordial leads V$_1$-V$_6$ show inverted T-waves, then the patient most likely has cardiac memory-induced T-wave inversion. ("Positive" here is selected, for example, to be represented as approximately 0.05 millivolts Microcomputer or computer platform 8040 includes a hardware unit 8041 which includes a central processing unit (CPU) 8042, a random access memory (RAM) 8043, and an input/output interface 8044. RAM 8043 is also called a main memory. Computer platform 8040 also typically includes an operating system 8045. In addition, a data storage device 8046 may be included. Storage device 8046 may include an optical disk or a magnetic tape drive or disk.

Various peripheral components may be connected to computer platform 8040, such as a terminal 8047, a keyboard 8048, and a printer 8049. Analog-to-digital (A/D) converter 8050 is used to sample an ECG signal. A/D converter 8050 may also provide amplification of the ECG signal prior to sampling.

Figure 7A:
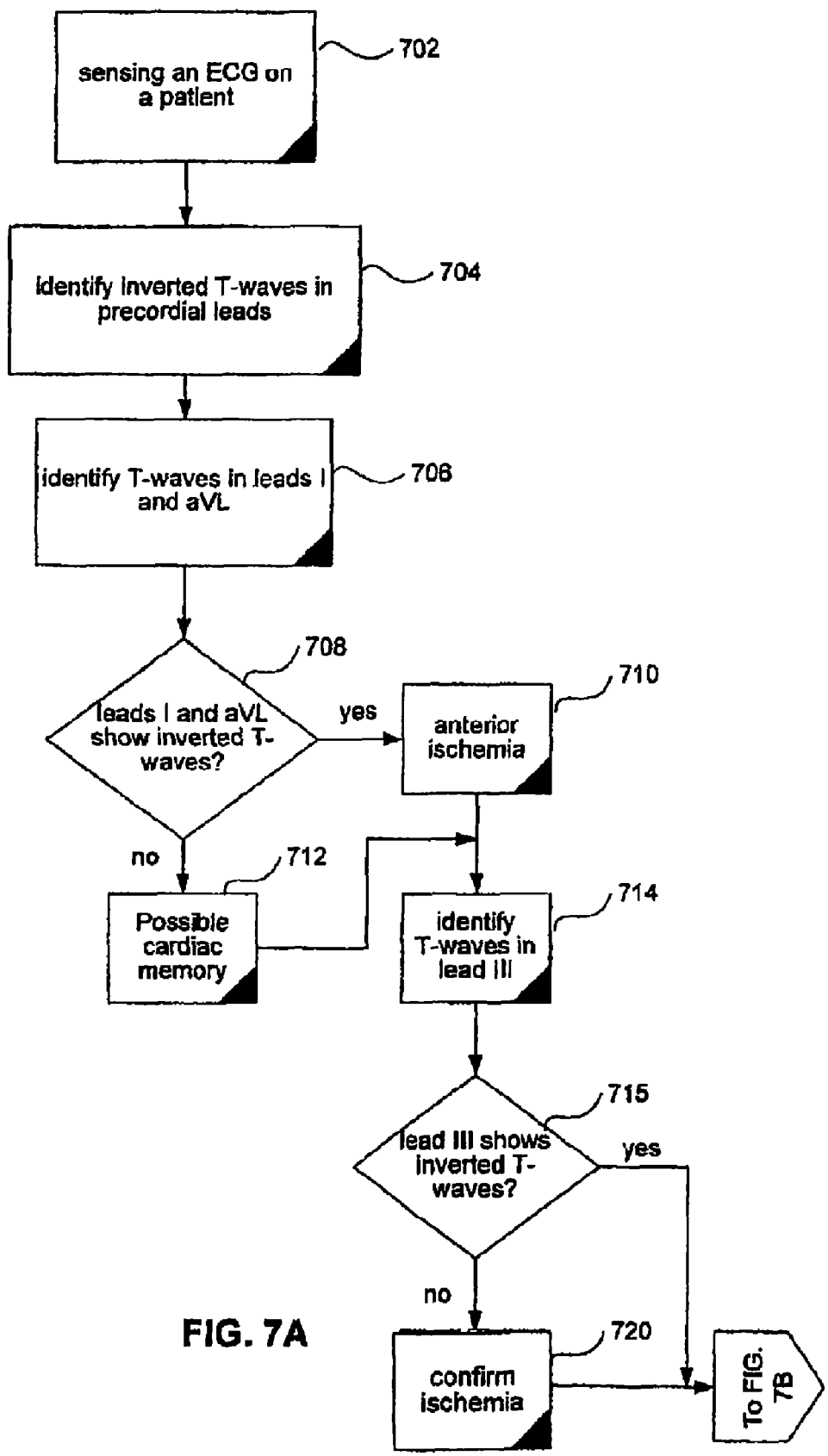
FIGS. 7A-7B illustrate an exemplary method of the present invention in flow chart form.
Figure 7B:
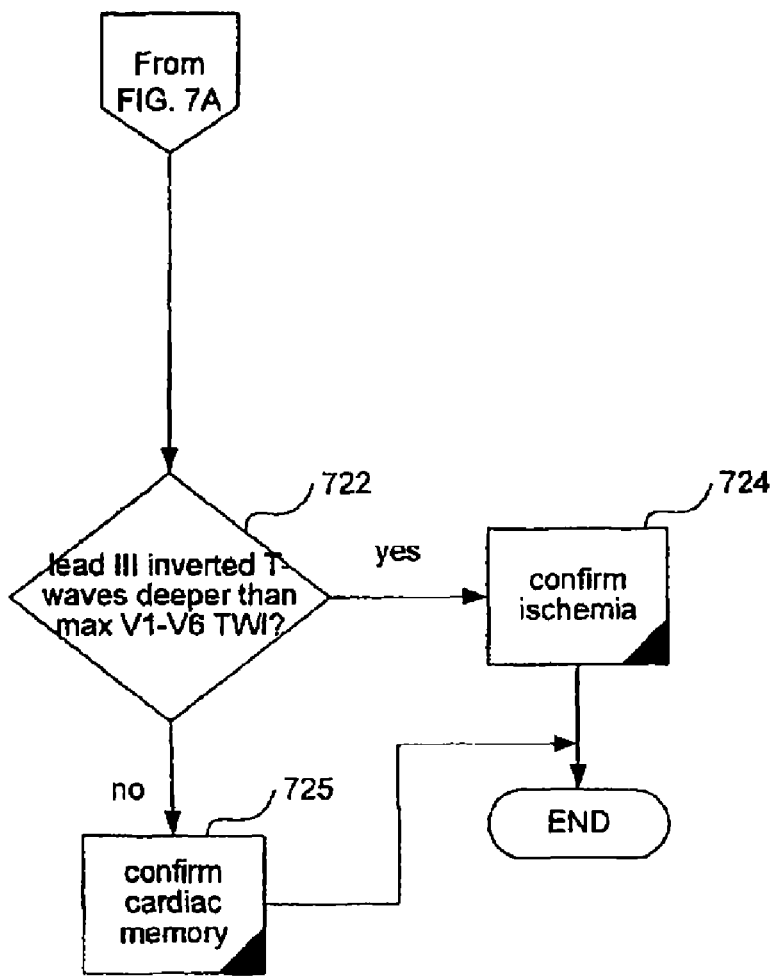

FIGS. 7A-7B illustrate an exemplary method of the present invention in flow chart form. As shown in FIGS. 7A-7B, step 702 includes sensing an electrocardiogram from a patient. Alternatively, pre-recorded data may be analyzed. Step 704 includes identifying inverted T-waves in at least some of precordial leads. Step 706 includes identifying T-waves in leads I and aVL. Steps 708-710 include diagnosing anterior ischemia if leads I and aVL show inverted T-waves. Step 712 includes diagnosing possible cardiac memory if the leads I and aVL show non-inverted T-waves. Optional step 714 includes identifying T-waves in lead III. Steps 715 and 720 include confirming ischemia diagnosis if the lead III does not show inverted T-waves. Optional steps 722-724 include confirming ischemic diagnosis if the lead III shows deeper inverted T-waves than maximum amplitude of precordial TWI. Step 725 includes confirming cardiac memory otherwise.

It is important to note that T-wave positivity in leads I and aVL is an active part of cardiac memory development, as an increase in T-wave amplitude is observed in the leads with a positive paced QRS complex (e.g., leads I and aVL).

The pattern of T-wave inversion in the inferior leads, if present, can also be useful in determining the etiology of TWI. Combined ECG changes in anterior and inferior leads can be present with wrap-around LAD ischemia. However, in that case, the T-wave vector maintains a rightward direction, causing more T-wave negativity in lead II compared to lead III, which is the opposite of the cardiac memory pattern.

As demonstrated previously in animal studies, the early stages of cardiac memory development can be accompanied by T vector rotation in the frontal plane before T-wave assumes the direction of pacing QRS complex. Drugs, such as calcium channel blockers and quinidine, affect development of cardiac memory and T vector shape. At the present time, the clinical relevance of these observations remains unclear.

In the above study, the site of the culprit lesion varied between the proximal and mid-LAD (below D1) and D1 alone. Intuitively, one would expect that a more lateral LV (left ventricle) spread of ischemia would result in a more rightward shift of the T-wave axis. Alternatively, with a distal LAD lesion perfusing only the apical-septal left ventricle, the rightward axis shift might be absent. The inventors did not observe differences in T-wave patterns between proximal and mid-LAD lesions, nor between lesions involving and not involving the D1 region. Therefore, there is no data to suggest that the location of LAD lesion by itself influences the degree of T-wave negativity in leads I and aVL. However, no patient in the ischemic group had distal LAD lesions, and the total number of patients in the study is insufficient to account for all possible variations of coronary anatomy.

Degree of ischemia is another potential factor contributing to the magnitude of T-wave changes. The majority of ischemic patients in the study had positive markers for myocardial injury, signifying severe ischemia. Conceivably, a lesser degree of ischemia could produce smaller T-wave changes. Counter-intuitively, when ischemic patients were divided into MB+ (myocardial branch (+)) and MB− (myocardial branch (−)) categories, no difference between the two groups was found in T-wave amplitude in the limb leads. Moreover, marker-negative patients had deeper precordial TWI than positive ones (see Table 4 above). This finding is in accord with observations in patients having myocardial infarction who demonstrate an inverse relationship between TWI magnitude, enzymatic size of MI (myocardial infarction) and functional recovery, suggesting that T-wave inversions indicate the presence of a viable stunned myocardium. Therefore, it seems unlikely that milder ischemia would alter the T-wave changes in ischemic patients.

Preliminary observations suggest that cardiac memory does not change the abnormal T vector associated with these conditions Cardiac memory development might be altered in patients with prior inferior myocardial infarction, presumably due to a lack of a viable myocardium adjacent to the pacing site.

It is also possible that the frontal plane T vector direction can be helpful in distinguishing between ischemic and non-ischemic (but other than cardiac memory) precordial TWI. Several studies using precordial ECG mapping showed that an I mapping pattern (inverted T-waves in the left upper quadrant with positive T-waves in the lower right quadrant) is highly predictive of ischemic TWI. Non-ischemic TWI were characterized by an N pattern (TWI in lower right quadrant and positive T-waves in left upper quadrant). These unipolar map patterns would likely correspond to positive (type N) and negative (type I) T-waves in bipolar leads I, aVL, as demonstrated in previously published ECGs.

Note that the present method may not help to separate repolarization changes associated with LVH, the most frequent confounder of ischemic changes, as they have similar frontal T-wave axis. Anterior wall ischemia is generally regarded as the most dangerous form of ischemia. Anterior wall ischemia is generally associated with LAD (left anterior descending) artery stenosis.

It should be noted that different locations of ischemia can result in different patterns of T-wave inversion. The present invention is particularly applicable to LAD ischemia, although it is also applicable, to other forms of ischemia. Of the three arteries in the heart—the LAD artery, the circumflex artery (LCX), and the right coronary artery (RCA)—in the case of LCX ischemia, sometimes there are negative T-waves in the precordial leads, and other times, not. Thus, it should be remembered that, compared to LAD ischemia, the frequency of TWI is less in the case of LCX ischemia. In approximately 40% of the cases, LCX ischemia is accompanied by T-wave inversion in the precordial leads.

In conclusion, the invention includes the advantage of differentiating precordial ischemic TWI from post-pacing TWI, based on the opposite directions of the frontal plane T-wave vectors. The inventors demonstrated that ischemic TWI is characterized by a rightward frontal plane T-wave axis, whereas in cardiac memory patients, the direction of the T vector points leftward. Bearing in mind these vector concepts, a simple discriminating rule has been devised, using standard 12-lead ECG criteria, which is easily applicable in everyday clinical practice. All cardiac memory patients and only one ischemic patient had positive T-wave in lead aVL. However, the single ischemic patient with positive T-wave in lead aVL showed a negative T-wave in lead I, a pattern not observed in cardiac memory patients. Therefore, the combination of: 1) positive T-wave in lead aVL and 2) non-inverted (positive or isoelectric) T-wave in lead I completely discriminated cardiac memory patients from ischemic patients. Using the most negative point in the T-wave was usually a better discriminator than using the frontal T-wave axis, which had minimal overlap between groups. This occurs because calculation of T-wave axis is based on the total T-wave area (negative and positive components) in a given lead, which in the case of biphasic T-waves dilutes the effect of terminal T-wave negativity.

By applying vectorcardiographic principles to interpretation of a standard 12-lead ECG, a simple algorithm was developed to discriminate between ischemic and post-pacing precordial TWI. Use of such vectorcardiographic information can significantly improve differential diagnosis of TWI.

It should also be appreciated that various modifications, adaptations, and alternative embodiments thereof may be made within the scope and spirit of the present invention. The invention is further defined by the following claims.

What is claimed is:

1. A method comprising the steps of:
   receiving, by a computing device, electrocardiographic data; and
   diagnosing non-ischemia T-wave abnormalities if a frontal plane T-wave vector associated with the electrocardiographic data is determined by the computing device to be leftward.

2. The method of claim 1, wherein the diagnosing non-ischemia step comprises:
   calculating by the computing device, from the electrocardiographic data, a direction of the frontal-plane T-wave vector; and
   diagnosing non-ischemia T-wave abnormalities if the direction of the frontal-plane T-wave vector is determined by the computing device to be between about 0 degrees and about −90 degrees.

3. The method of claim 1, wherein the diagnosing non-ischemia step comprises:
   identifying by the computing device, from the electrocardiographic data, T-waves in leads I and aVL; and
   diagnosing non-ischemia T-wave abnormalities if the leads I and aVL are determined by the computing device to not show inverted T-waves.

4. The method of claim 3, wherein the diagnosing non-ischemia step comprises:
   identifying by the computing device, from the electrocardiographic data, T-waves in lead III;
   determining by the computing device that the T-waves in lead III show inverted T-waves; and
   diagnosing non-ischemia T-wave abnormalities if lead III is determined by the computing device to show inverted T-waves that are not deeper than maximal precordial (leads V1-V6) T-wave inversion.

5. A system comprising:
   means for receiving electrocardiographic data; and
   means for diagnosing non-ischemia T-wave abnormalities if a frontal plane T-wave vector associated with the electrocardiographic data is leftward.

6. The system of claim 5, wherein the diagnosing means comprises:
   means for calculating, from the electrocardiographic data, a direction of the frontal plane T-wave vector; and
   means for diagnosing non-ischemia T-wave abnormalities if the direction of the frontal plane T-wave vector is between about 0 degrees and about −90 degrees.

7. The system of claim 5, wherein the diagnosing means comprises:
   means for identifying, from the electrocardiographic data, T-waves in leads I and aVL; and
   means for diagnosing non-ischemia T-wave abnormalities if the leads I and aVL do not show inverted T-waves.

8. The system of claim 7, wherein the diagnosing means comprises:
   means for identifying, from the electrocardiographic data, T-waves in lead III;
   means for determining that the T-waves in lead III show inverted T-waves; and
   means for diagnosing non-ischemia T-wave abnormalities if lead III is determined to show inverted T-waves that are not deeper than maximal precordial (leads V1-V6) T-wave inversion.

9. A tangible computer-readable medium having stored thereon, computer-executable instructions that, if executed by a computing device, perform a method comprising the steps of:
   receiving electrocardiographic data; and
   diagnosing non-ischemia T-wave abnormalities if a frontal plane T-wave vector associated with the electrocardiographic data is determined to be leftward.

10. The tangible computer-readable medium of claim 9, wherein the diagnosing non-ischemia step comprises:
    calculating from the electrocardiographic data, a direction of the frontal plane T-wave vector; and
    diagnosing non-ischemia T-wave abnormalities if the direction of the frontal plane T-wave vector is determined to be between about 0 degrees and about −90 degrees.

11. The tangible computer-readable medium of claim 9, wherein the diagnosing non-ischemia step comprises:
    identifying from the electrocardiographic data, T-waves in leads I and aVL; and
    diagnosing non-ischemia T-wave abnormalities if the leads I and aVL are determined to not show inverted T-waves.

12. The tangible computer-readable medium of claim 11, wherein the diagnosing non-ischemia step comprises:
    identifying from the electrocardiographic data, T-waves in lead III;
    determining that the T-waves in lead III show inverted T-waves; and
    diagnosing non-ischemia T-wave abnormalities if lead III is determined to show inverted T-waves that are not deeper than maximal precordial (leads V1-V6) T-wave inversion.

* * * * *